United States Patent [19]

Kitamura et al.

[11] Patent Number: 4,839,195

[45] Date of Patent: Jun. 13, 1989

[54] COATING BLADE FOR MICROTOME AND METHOD FOR THE PREPARATION THEREOF

[75] Inventors: Hajime Kitamura, Chiba; Tamaki Iida, Tokyo, both of Japan

[73] Assignee: Shin-Etsu Chemical Co., Ltd., Tokyo, Japan

[21] Appl. No.: 157,091

[22] Filed: Feb. 9, 1988

Related U.S. Application Data

[63] Continuation of Ser. No. 869,905, Jun. 3, 1986, abandoned.

[30] Foreign Application Priority Data

Jun. 28, 1985 [JP]  Japan ................................ 60-141815

[51] Int. Cl.$^4$ ............................................. B05D 3/06
[52] U.S. Cl. ........................................ 427/38; 427/377
[58] Field of Search ................................... 427/38, 377

[56] References Cited

U.S. PATENT DOCUMENTS

| | | | |
|---|---|---|---|
| 4,416,912 | 11/1983 | Bache | 427/50 X |
| 4,485,706 | 12/1984 | Disharoon | 83/42 |
| 4,504,519 | 3/1985 | Zelez | 427/39 |
| 4,629,373 | 12/1986 | Hall | 428/408 X |

*Primary Examiner*—Bernard Pianalto
*Attorney, Agent, or Firm*—Wenderoth, Lind & Ponack

[57] ABSTRACT

A microtome blade made of, for example, sapphire is imparted with greatly improved cutting power as well as durability and anti-corrosion resistance by providing a coating layer of diamond thereon. Such a coating layer can be formed by subjecting a base blade to a treatment of plasma-induced chemical vapor deposition of diamond in an atmosphere of a gaseous mixture of a hydrocarbon compound and hydrogen followed by a heat treatment at 700°–1300° C. to expel any adsorbed impurities in the diamond layer.

4 Claims, No Drawings

COATING BLADE FOR MICROTOME AND METHOD FOR THE PREPARATION THEREOF

This application is a continuation of now abandoned application Ser. No. 869,905 filed June 3, 1986.

BACKGROUND OF THE INVENTION

The present invention relates to a coated blade for microtome or, more particularly, to a coated blade for microtome having markedly improved durability, anti-corrosion resistance and cutting power and a method for the preparation thereof with high productivity.

Along with the progress in the medical and biological sciences in recent years, the importance of microscopic investigations is increasing more and more and many fine results are obtained as a consequence of the improvements in the performance of optical and electron microscopes and in related techniques. Needless to say, microscopic study of medical and biological materials is performed in many cases with a specimen of an extremely thin sliced section of the living body tissue prepared by use of a microtome and having a thickness of, for example, 50 to 100 nm. Various materials are used for the preparation of blades mounted on a microtome for such a purpose including metals, glass, sapphire and diamond. Microtome blades prepared of these materials and used as such have their respective disadvantages and problems. For example, metal-made microtome blades must have the edge redressed after each time of their use. Glass-made microtome blades are usually throwaway or disposable and any blade once used must be replaced with a new one having an acutely angled sharp edge newly formed by breaking a glass plate at the sacrifice of the efficiency of the microscopic examination works. Moreover, glass-made microtome blades must be prepared by the operator himself of the microscopes and still no reliable and reproducible results can be expected in each preparation. Sapphire-made microtome blades have relatively poor cutting power and durability for their expensiveness in comparison with metal- and glass-made blades. Diamond blades are, even though the performance as a blade may be satisfactory, very expensive because they are manufactured by handicraft of highly skilled artisans with low productivity.

In addition, some of the conventional microtome blades have a problem that striation or chatter marks appear on the sliced specimen therewith so that they are not always suitable for use in high-grade investigations in the medical and biological sciences. While it is not rare that the microscopic examination in the fields of recent medical and biological sciences requires an extremely thin sliced specimen having a thickness of 50 nm or smaller, in particular, such a thin specimen can hardly be prepared by use of conventional microtome blades with reliableness.

SUMMARY OF THE INVENTION

The present invention therefore has an object to provide a blade for microtome free from the above described problems and disadvantages in the conventional microtome blades.

The microtome blade of the present invention is a blade having a specific coating layer on a base blade. Namely, the blade for microtome of the invention comprises:

(a) a base blade; and
(b) a coating layer of diamond formed on the base blade.

The diamond-coated microtome blade mentioned above can be prepared by subjecting a base blade of glass, metal or ceramic to a treatment of plasma-induced vapor-phase deposition in an atmosphere of a gaseous mixture composed of a hydrocarbon compound and hydrogen to form a layer of diamond in a thin layer deposited on the surface of the base blade and then subjecting the blade coated with the layer of diamond to a heat treatment at 700° to 1300° C. so as to upgrade the diamond layer by removing the impurities contained therein and increasing the adhesion between the base blade and the diamond layer.

DETAILED DESCRIPTION OF THE PREFERRED EMBODIMENTS

As is described above, the microtome blade of the invention is characterized by the coating layer of diamond formed on a base blade as the substrate and, by virtue of the wearing resistance, anti-corrosion resistance and extremely high hardness inherent in diamond, the coated microtome blade of the invention is imparted with greatly improved durability, anti-corrosion resistance and cutting power in comparison with conventional microtome blades.

The base blade as the substrate of coating is not particularly limitative in respect of the material provided that the material can withstand the plasma-induced vapor-phase deposition and subsequent heat treatment and may be made of any of the same materials as in conventional microtome blades including metallic materials such as stainless steel and hard metals, glass, sapphire and the like. The coating layer of diamond formed on the base blade should have a thickness in the range from 5 to 50 nm or, preferably, from 8 to 20 nm since the reliability of the effect obtained by the coating would be low when the thickness of the coating layer is too small while a microtome blade provided with a coating layer having a thickness larger than 50 nm is not suitable for the preparation of an extremely thin sliced section for microscopic examination. The diamond layer may contain graphite though in a limited amount.

Like conventional microtome blades, the inventive diamond-coated microtome blade also has a wedge-like configuration as a whole and the coating layer of diamond is formed on both surfaces of the base blade intersecting on the edge line. The base blade made of a metal, glass, sapphire and the like material should have a sufficiently sharp edge making an acute angle. The coating layer of diamond should preferably have a smallest thickness on the edge with gradually increasing thickness with the increase of the distance from the edge in order that the blade may have good cutting power.

The above mentioned coating layer of diamond can be formed by several different methods but a convenient method is to utilize the process of plasma-induced chemical vapor-phase deposition. Thus, the base blade is subjected to a treatment of plasma-induced chemical vapor-phase deposition in an atmosphere of a gaseous mixture composed of a hydrooarbon compound and hydrogen as diluted, if necessary, by a carrier gas such as helium, argon and the like so that the hydrocarbon gas is decomposed and deposited in the form of diamond, which may contain a small amount of graphite, as a coating film on the surface. The method of plasma-induced vapor-phase deposition includes those by use of high frequency, direct current and microwave power sources as well as a method in which a metal-made heater coil is installed in the atmosphere of plasma and a method of ion-beam vapor-phase deposition. The electric power should preferably have a high frequency in the microwave range of at least 30 MHz. Suitable hydrocarbon compounds include methane, ethane, propane, ethylene and the like.

The plasma-induced chemical vapor-phase deposition of diamond on a base blade is performed by placing the base blade in a plasma chamber and, while the pressure inside the plasma chamber is kept in the range from 0.0027 to 2.7 kPa (0.02 to 20 mmHg) by continuously introducing a gaseous mixture of a hydrocarbon compound and hydrogen together with or without a carrier gas such as helium and argon, by generating plasma inside the plasma chamber with impression of a microwave electric power at a frequency of, for example, 2.45 GHz between the electrodes installed inside the chamber. The hydrocarbon compound and hydrogen should be mixed in a mixing ratio in the range from 0.2:99.8 to 10:90 by volume. The base blade should be hetted and kept at a temperature in the range, preferably, from 850 to 1050° C. The hydrocarbon compound is then decomposed in the plasma atmosphere and deposited in the form of diamond to form a thin coating layer on the surface of the base blade. The coating layer of diamond may contain a small amount of graphite depending on the conditions. The vapor-phase deposition is continued until the thickness of the coating layer has reached a desired value.

The coating layer of diamond thus deposited may contain hydrogen, carbon-hydrogen radicals and the like adsorbed therein so that it is essential to subject the diamond-coated blade to a heat treatment in an inert atmosphere at a temperature in the range from 700 to 1300° C. or, preferably, from 950 to 1300° C. for a length of time, for example, from 0.5 to 1.5 hours to remove the above mentioned impurities. The thus obtained diamond-coated blade is useful for mounting on a microtome with markedly improved durability, wearing resistance and cutting power. Moreover, the coated microtome blade of the invention can be manufactured with high industrial productivity to overcome the problems of low productivity in the manufacture of conventional diamond blades by handworks.

In the following, the diamond-coated microtome blade of the invention is illustrated in more detail by way of an example. Example.

A blade of synthetic sapphire prepared by machine-working in the form of a microtome blade was washed with pure water and isopropyl alcohol followed by drying and then mounted on a substrate stand in a plasma chamber having a waveguide opening, a pair of plungers and a gas inlet nozzle. The blade was mounted in such a manner that the direction of the gas flow inside the chamber was in parallel to the bisector plane of the angle made of the two surfaces intersecting on the edge line of the blade.

After evacuation of the plasma chamber down to a pressure of about 5 Pa, a 1:10 by volume mixture of methane and hydrogen was continuously introduced into the chamber and the pressure inside the chamber was controlled and maintained at about 10 Pa by the balance with continuous evacuation. While keeping the above described atmospheric conditions, microwaves at a frequency of 2.45 GHz as generated by a magnetron were led by a waveguide to a quartz glass-made reactor tube through an isolator, power motor and three-stub tuner so that plasma discharge was caused around the substrate blade. The temperature of the substrate blade was kept at about 930° C. when the electric power input was 300 watts. After about 4 minutes of the plasma treatment in the above described manner, the blade was taken out of the plasma chamber and examined to find that the surface of the sapphire blade was coated with a thin layer having a thickness of about 10 to 15 nm.

The thus coated sapphire blade taken out of the plasma chamber was then heated in a furnace under an inert atmosphere of argon at 1200° C. for 30 minutes followed by annealing with gradual temperature decrease. The X-ray diffractometric examination of the coating layer revealed that it had a crystalline structure of diamond and the coating layer was free from any defects insofar as the result of the inspection by use of an optical microscope indicated. An infrared absorption spectroscopy was undertaken of the coating layer of diamond for the inrared absorption bands by the C-H linkages before and after the heat treatment at 1200° C. The results were that the absorption bands which had been clearly recognized before the heat treatment disappeared almost completely indicating the effectiveness of the heat treatment.

The above described diamond-coated sapphire blade and a conventional diamond-made microtome blade for comparative purpose were subjected to the cutting test by slicing an internal organ of an animal fixed with an epoxy resin as the object body to prepare thin sections of each about 30 nm thickness. The results were that the cutting power of the diamond-coated microtome blade of the invention was almost as sharp as before use even after preparation of 500 pieces of thin microscopic specimens while the conventional diamond blade could no longer be used after preparation of about 300 pieces of the microscopic specimens.

What is claimed is:

1. A method for the preparation of a microtome blade coated with a layer of diamond which comprises the steps of:
    (a) subjecting a base blade to a treatment of plasma-induced chemical vapor deposition of diamond by exposing the same to an atmosphere of plasma generated in a gaseous mixture composed of a hydrocarbon compound and hydrogen; and
    (b) subjecting the base blade thus coated with a layer of diamond to a heat treatment at a temperature in the range from 700 to 1300° C. for a length of time in the range from 0.5 to 1.5 hours in an inert atmosphere.

2. The method for the preparation of a microtome blade coated with a layer of diamond as claimed in claim 1 wherein the gaseous mixture is composed of a hydrocarbon compound and hydrogen in a ratio from 0.2:99.8 to 10:90 by volume.

3. The method for the preparation of a microtome blade coated with a layer of diamond as claimed in claim 1 wherein the hydrocarbon compound is selected from the group consisting of methane, ethane, propane and ethylene 4. The method for the preparation of a microtome blade coated with a layer of diamond as claimed in claim wherein the gaseous mixture of the hydrocarbon compound and hydrogen has a pressure in the range from 0.0027 to 2.7 kPa.

* * * * *